(12) United States Patent
Wells et al.

(10) Patent No.: US 7,452,335 B2
(45) Date of Patent: Nov. 18, 2008

(54) METHOD AND APPARATUS FOR THE DETECTION OF NEUROMUSCULAR DISEASE USING DISEASE SPECIFIC EVOKED NEUROMUSCULAR RESPONSE ANALYSIS

(75) Inventors: Martin D. Wells, Needham, MA (US); Shai N. Gozani, Brookline, MA (US)

(73) Assignee: NeuroMetrix, Inc., Waltham, MA (US)

( * ) Notice: Subject to any disclaimer, the term of this patent is extended or adjusted under 35 U.S.C. 154(b) by 334 days.

(21) Appl. No.: 10/288,852

(22) Filed: Nov. 6, 2002

(65) Prior Publication Data

US 2003/0093006 A1    May 15, 2003

Related U.S. Application Data

(60) Provisional application No. 60/332,884, filed on Nov. 6, 2001.

(51) Int. Cl.
*A61B 5/05* (2006.01)
*A61B 5/04* (2006.01)

(52) U.S. Cl. .................................. 600/554; 600/546

(58) Field of Classification Search ................ 600/546, 600/547, 554; 607/48
See application file for complete search history.

(56) References Cited

U.S. PATENT DOCUMENTS

| | | | |
|---|---|---|---|
| 4,314,379 A | | 2/1982 | Tanie et al. |
| 4,807,643 A | | 2/1989 | Rosier |
| 4,964,411 A | | 10/1990 | Johnson et al. |
| 5,092,343 A | | 3/1992 | Spitzer et al. |
| 5,131,401 A | | 7/1992 | Westenskow et al. |
| 5,264,459 A | * | 11/1993 | Chelmicka-Schorr et al. ............... 514/646 |
| 5,327,902 A | | 7/1994 | Lemmen |
| 5,505,208 A | * | 4/1996 | Toomim et al. ............ 600/546 |
| 5,540,235 A | * | 7/1996 | Wilson ....................... 600/554 |
| 5,662,118 A | * | 9/1997 | Skubick ..................... 600/546 |
| 5,697,369 A | | 12/1997 | Long, Jr. et al. |
| 5,813,993 A | | 9/1998 | Kaplan et al. |
| 5,916,172 A | * | 6/1999 | Hodges et al. ............. 600/546 |
| 6,132,386 A | * | 10/2000 | Gozani et al. .............. 600/554 |
| 6,366,806 B1 | * | 4/2002 | Yaar .......................... 600/546 |
| 6,379,313 B1 | | 4/2002 | Gozani et al. |

OTHER PUBLICATIONS

Iyer VG. Understanding nerve conduction and electromyography studies. Hand Clin. May 1993;9(2):273-87.*
Fang F, Ng V. Use of neural network analysis to diagnose breast cancer patients. IEEE Tencon. 1993:841-844.*
Pattichis CS, Schizas CN, Middleton LT. Neural network models in EMG diagnosis. IEEE Trans Biomed Engr. May 1995;42(5):486-496.*
Bischoff C, Stalberg E, Falck B, Puksa L. Significance of A-waves recorded in routine motor nerve conduction studies. Electroencephalogr Clin Neurophysiol. Dec. 1996;101(6):528-33.*

* cited by examiner

*Primary Examiner*—Max Hindenburg
*Assistant Examiner*—Michael Apanius
(74) *Attorney, Agent, or Firm*—Pandiscio & Pandiscio (57) ABSTRACT

A method and apparatus for assessing neuromuscular pathology in an individual, by (a) applying a plurality of stimuli to a peripheral nerve; (b) recording from the peripheral nerve, or from a muscle innervated by the peripheral nerve, at least one response to each stimulus; (c) processing each response into at least one response characteristic; (d) compiling the response characteristics from all of the responses into a plurality of descriptive parameters of the response characteristics; and (e) analyzing the plurality of descriptive parameters according to a function specific to the neuromuscular pathology so as to yield an indicator of the pathology.

6 Claims, 10 Drawing Sheets

STEP 1:
APPLYING A PLURALITY OF STIMULI TO A PERIPHERAL NERVE

STEP 2:
RECORDING FROM THE PERIPHERAL NERVE, OR FROM A MUSCLE INNERVATED BY THE PERIPHERAL NERVE, AT LEAST ONE RESPONSE TO EACH SAID STIMULUS

STEP 3:
PROCESSING EACH SAID RESPONSE INTO AT LEAST ONE RESPONSE CHARACTERISTIC

STEP 4:
COMPILING SAID RESPONSE CHARACTERISTICS FROM ALL OF SAID RESPONSES INTO A PLURALITY OF DESCRIPTIVE PARAMETERS OF SAID RESPONSE CHARACTERISTICS

STEP 5:
ANALYZING SAID PLURALITY OF DESCRIPTIVE PARAMETERS ACCORDING TO A FUNCTION SPECIFIC TO THE NEUROMUSCULAR PATHOLOGY SO AS TO YIELD AN INDICATOR OF THE PATHOLOGY

FIG. 4

STEP 1:
RECORDING, FROM A PERIPHERAL NERVE, OR FROM A MUSCLE INNERVATED BY A PERIPHERAL NERVE, A PLURALITY OF RESPONSES EVOKED BY A PLURALITY OF STIMULI DELIVERED TO THE PERIPHERAL NERVE

STEP 2:
PROCESSING EACH OF SAID RESPONSES INTO AT LEAST ONE RESPONSE CHARACTERISTIC

STEP 3:
COMPILING SAID RESPONSE CHARACTERISTICS FROM ALL OF SAID RESPONSES INTO A PLURALITY OF DESCRIPTIVE PARAMETERS

STEP 4:
REPEATING STEPS (1), (2) AND (3) ON A PLURALITY OF INDIVIDUALS WITHOUT THE NEUROMUSCULAR PATHOLOGY TO GENERATE A FIRST SET OF SAID DESCRIPTIVE PARAMETERS

STEP 5:
REPEATING STEPS (1), (2) AND (3) ON A PLURALITY OF INDIVIDUALS WITH THE NEUROMUSCULAR PATHOLOGY SO AS TO GENERATE A SECOND SET OF DESCRIPTIVE PARAMETERS

STEP 6:
PROCESSING SAID FIRST SET OF DESCRIPTIVE PARAMETERS AND SAID SECOND SET OF DESCRIPTIVE PARAMETERS SO AS TO DETERMINE A FUNCTION OF SAID DESCRIPTIVE PARAMETERS THAT IS INDICATIVE OF THE NEUROMUSCULAR PATHOLOGY

Table 1. Peroneal and Tibial Nerve Height Normalization Factors Determined by Least Squares Linear Regression of Control Group Data

| Nerve | Parameter | Height Normalization Factor (msec/cm) | $R^2$ § |
|---|---|---|---|
| Peroneal | F-wave Latency* | 0.400 | 0.547 |
| | DML† | 0.014 | 0.053 |
| Tibial | F-wave Latency* | 0.397 | 0.602 |
| | DML† | 0.023 | 0.141 |

\* Height dependence of F-wave latencies determined by linear regression between all acquired F-wave latencies from control group and height of corresponding subjects; peroneal nerve (N=1860 latencies), tibial nerve (N=2730 latencies).
† Height dependence of DMLs determined by linear regression between mean DML and subject height for each subject.
§ $R^2$, variance in F-wave latencies explained by subject height; approximately 55% of the variance in peroneal F-wave latency in control subjects is attributable to height, 5% peroneal DML, 60% tibial F-wave latency, 14 % tibial DML.

FIG. 7

Table 2: Demographic, Clinical, and MRI Features of Study Groups

|  | Control* | L5/S1 Compression† |
|---|---|---|
| No. of Subjects | 35 | 25 |
| Age‡ | 32.7 (8) | 37.4 (8.1) |
| Height (cm)‡ | 172.2 (10.4) | 171.7 (8.13) |
| Female (%) | 34.3 | 48 |
| Low back pain (%)§ | 0 | 84 |
| Left as most symptomatic limb (%)§ | – | 56 |
| Straight leg raise (%)¶ | – | 68 |
| Diminished patellar reflex (%)¶ | – | 8 |
| Diminished ankle reflex (%)¶ | – | 44 |
| Sensory loss (%)¶ | – | 32 |
| Weakness (%)¶ | – | 28 |
| L5 compression / isolated L5 (%)‖ | – | 64/36 |
| L5 compression severe (%)‖ | – | 25 |
| S1 compression / isolated S1 (%)‖ | – | 64/36 |
| S1 compression severe (%)‖ | – | 37.5 |

\* Asymptomatic subjects, no history of spine surgery, lower extremity neuromuscular disorders or radiculopathy.

† MRI confirmed L5 and/or S1 root compression, lower extremity symptoms consistent with root involvement. Only those subjects for whom electrophysiological results were obtained are included.

‡ Mean (standard deviation)

§ Low back pain and symptomatic limb as reported by subject on questionnaire.

¶ Straight leg raise, reflexes, sensory loss and weakness determined on physical exam of subject. Positive straight leg raise if increase in distal leg symptoms with hip flexion. Diminished reflexes if less then 2+ using standard clinical methods. Weakness graded as positive if encountered on dorsiflexion , plantarflexion, eversion or inversion of the foot.

‖ Based on MRI imaging of lumbosacral spine at L3-L4 through L5-S1 intervertebral disc space levels. Isolated percentage refers to number of patients for which only the L5 or S1 roots were involved. Severe percentage refers to the number of patients with grade III root compression (see Methods).

FIG. 8

Table 3: Comparison of Nerve Conduction Parameters in Control and L5/S1

| Nerve Conduction Parameter | Peroneal Nerve | | Tibial Nerve | |
|---|---|---|---|---|
| | Control | L5/S1 ompression | Control | L5/S1 )mpression† |
| F-wave Parameters | | | | |
| Minimum (msec)† | 46.61 (2.93) | 48.78 (4.52) | 45.67 (3.15) | 47.07 (5.83) |
| Mean (msec) † | 50.02 (2.79) | 54.37 (4.54) * | 49.11 (3.05) | 52.53 (2.64) * |
| Maximum (msec)† | 55.43 (6.00) | 63.22 (10.78) * | 53.10 (4.81) | 56.50 (4.19) * |
| Persistence (%)† | 66.4 (25.6) | 47.2 (29.5) * | 97.5 (6.6) | 90.5 (18.0) |
| CMAP | | | | |
| DML (msec) † | 3.92 (0.60) | 3.95 (1.15) | 4.18 (0.61) | 4.64 (0.64) * |
| Amplitude (mV) † | 8.74 (3.85) | 6.12 (4.70) | 14.25 (6.45) | 9.60 (5.04) * |

† Mean (standard deviation). Minimum, mean and maximum F-wave latencies and DML (distal motor y) normalized to a common subject height of 172 cm.
* Statistically significant difference between the control and L5/S1 compression groups as ined by a two-sample t-test at a significance level of 0.005.

FIG. 9

Table 4: Accuracy of Electrophysiological Predictors of L5/S1 Root Compression

| Predictor | Sensitivity* | Area Under ROC Curve§ | Odds Ratio¶ |
|---|---|---|---|
| Peroneal F-wave Latency, minimum (95% CI)† | 29.2 (12.5 – 50.0) | 0.60 (0.51 – 0.73) | 1.00 (1.00 – 1.00) |
| NC-Composite (95% CI)‡ | 87.5 (56.3 – 100.0) | 0.91 (0.84 – 0.97) | 6.81 (3.29 – 18.09) |

† Minimum peroneal nerve F-wave latency used as performance standard.
‡ Composite nerve conduction measurement based on the following F-wave latency parameters: peroneal mean, peroneal $7^{th}$ decile, tibial mean, tibial $1^{st}$ decile, tibial maximum. Later two parameters are negatively predictive.
\* Sensitivity at fixed specificity of 85%.
§ ROC, receiver-operating characteristic.
¶ Odds ratio for correct diagnostic classification of L5/S1 root compression by ROC analysis. Normalized to ROC of minimum peroneal F-wave latency.

FIG. 10

METHOD AND APPARATUS FOR THE DETECTION OF NEUROMUSCULAR DISEASE USING DISEASE SPECIFIC EVOKED NEUROMUSCULAR RESPONSE ANALYSIS

REFERENCE TO PENDING PRIOR PATENT APPLICATION

This patent application claims benefit of pending prior U.S. Provisional Patent Application Ser. No. 60/332,884, filed Nov. 6, 2001 by Martin D. Wells et al. for APPARATUS AND METHOD FOR DETECTION OF NEUROMUSCULAR DISEASE USING DISEASE SPECIFIC EVOKED NEUROMUSCULAR RESPONSE ANALYSIS, which patent application is hereby incorporated herein by reference.

FIELD OF THE INVENTION

This invention relates to neuromuscular disease in general, and more particularly to methods and apparatus for the detection of the same.

BACKGROUND OF THE INVENTION

Muscle tissue, like nerve tissue, is electrically active and, when elicited, produces a voltage response which can be recorded.

More particularly, when a motor nerve is electrically stimulated above a certain threshold, an action potential will propagate distally to the muscle innervated by the nerve. The response recorded over that muscle is called a "compound muscle action potential" (or "CMAP"). This measured muscle response is also sometimes referred to as an "M-wave".

Figure 1:
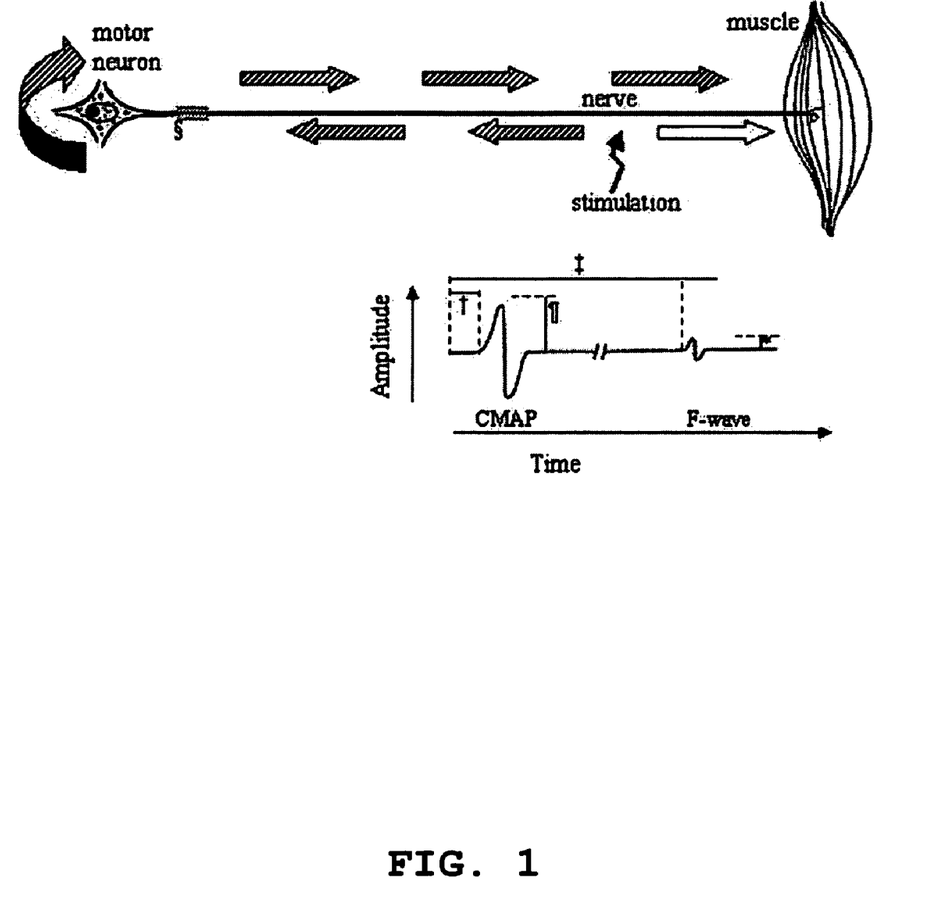
FIG. 1 illustrates a schematic of a representative motor nerve conduction study. The stimulation of a peripheral motor nerve evokes a direct orthodromic impulse (open arrow) as well as an antidromic impulse (shaded arrows) that propagates to the corresponding motor neuron cell body and then returns orthodromically if backfiring occurs. Direct orthodromic activation evokes a compound muscle action potential (CMAP) that is characterized by a latency (†) and an amplitude (¶). Antidromic impulses, for which motor neuron backfiring occurs, generate an F-wave that is also characterized by a latency (‡) and an amplitude (*) F-waves are generated following action potential propagation along the entire length of the nerve including, specifically, propagation through the nerve root (§).

In other words, and looking now at FIG. 1, the CMAP is generated by conduction of the neural impulse from the point of stimulation directly to the innervated muscle (open arrow) and is typically characterized by a latency period (†) and an amplitude (¶).

In addition to a nerve action potential propagating distally towards the muscle (orthodromically), an electrical stimulation will also elicit an action potential which propagates proximally (antidromically) along a motor fiber until it reaches the motor neurons in the spinal cord. There, the potential exists for activated motor neurons to backfire, producing a reflected action potential that propagates orthodromically towards the innervated muscle(s) and causes a second muscle response. The measured muscle response associated with this backfiring is called an "F-wave". The F-wave is part of a class of neuromuscular responses known as "late responses".

In other words, and still looking now at FIG. 1, the F-wave response is generated by antidromic action potential propagation along motor nerve axon(s) (shaded arrows) beginning at the point of stimulation, passing through the ventral root(s) of the spinal column to the motor neuron cell body in the spinal cord, backfiring of the motor neurons, and then orthodromic conduction back to the innervated muscle. An individual F-wave response is normally characterized by a number of attributes including latency (‡) and amplitude (*).

In this respect it should be appreciated that F-wave latency is defined as the time difference between the stimulus and the initial deflection of the F-wave response signal from baseline. While other descriptors of F-waves (e.g., amplitude, duration, area, morphology, etc.) are also believed to embody clinically useful information, the F-wave latency (and parameters derived from the F-wave latency) has generally been the most common attribute studied in clinical neurophysiology studies.

Since only a small fraction of the motor neurons backfire, and since the backfiring motor neurons may be different for each stimulus, the F-wave amplitude is, on average, less than 10% that of a CMAP. In addition, the F-wave also occurs much later than the CMAP, since the F-wave is initiated by nerve action potentials that have propagated along a longer path of nerve. F-waves can be recorded with electrodes placed directly on the surface of the skin. When recording electrodes are placed sufficiently adjacent to the activated muscle (such as directly over the muscle motor point), recordings are generally designated "on-muscle". Recordings can also be made with electrodes place away from the activated muscle. These latter recordings are generally designated "volume-conducted".

Figure 2:
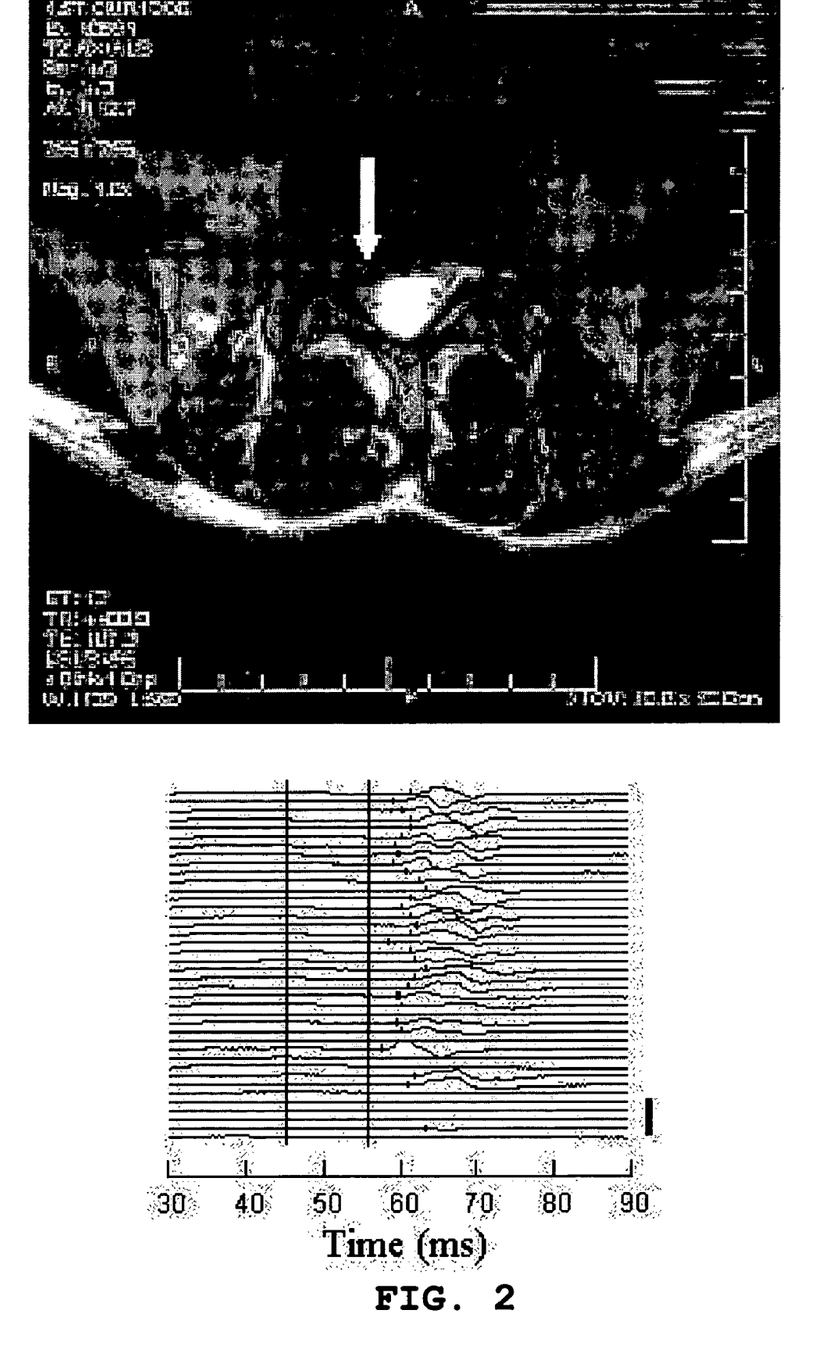

Inasmuch as the backfiring motor neurons are different from stimulus to stimulus, two F-wave recordings will rarely be the same even when identical stimuli and recording electrodes are used. Furthermore, in some instances no neurons will backfire and hence the recorded signal will contain no F-wave response. Thus, for example, in FIG. 2 there is shown a raster of 12 F-wave signals, demonstrating differences between the F-wave responses in different sweeps.

In other words, inasmuch as the probability of any given motor neuron backfiring in response to nerve stimulation is low, the number of impulses propagating back down the nerve, and the resulting F-wave response amplitude, are small and highly variable. In addition, because F-wave responses represent a sampling of the spinal motor neuron pool, sequential F-wave responses tend to differ in latency, amplitude, morphology and, indeed, even whether they are present from one stimulus to the next.

Various neuropathologies can alter both CMAP and F-wave responses. As a result, analyzing CMAP and F-wave responses can be useful in detecting such neuropathology.

More particularly, changes in the amplitude, morphology, or latency of the CMAP generally indicate distal disease, although proximal pathology causing axonal loss can prolong the distal latency and decrease the CMAP amplitude.

The F-wave response reflects conduction along the entire length of the nerve and is thus diagnostically sensitive to nerve root compromise, proximal nerve compression, distal nerve entrapment syndromes, plexopathies, and systemic neuropathies.

More particularly, in a typical nerve conduction study, the nerve is stimulated a number of times and the resulting CMAP and F-wave responses are collected and analyzed. The CMAP generally responds in a highly consistent manner from one stimulus to the next so that an attribute such as latency can be reported as a single value appropriate to all collected signals. By contrast, the attributes of sequential F-wave responses vary. Hence an attribute of the collection of F-wave responses is most appropriately reported as a frequency distribution or as a probability density function. Traditional nerve conduction studies typically report only one F-wave distribution parameter, i.e., the minimum F-wave latency, which is the earliest latency among all recorded F-wave responses. This parameter characterizes conduction of the nerve fibers with the fastest propagation velocities. Other F-wave parameters which have been used include the mean latency among all the F-wave responses, the maximum latency, the median latency, the range of latencies, and the percentage of stimuli evoking detectable F-wave responses (i.e., "persistence")

F-waves have certain advantages over the CMAP in clinical neurophysiology studies since their associated nerve potentials propagate through a longer stretch of nerve. This is especially true for distinguishing systematic nerve diseases (such as diabetic neuropathy) from localized nerve diseases (such as carpal tunnel syndrome). However, the clinical utilities of F-waves are often limited by the uncertainty of their occurrence, the variability of their morphology and poor signal quality (i.e., noise and baseline drift). This is especially true for "volume-conducted" F-wave recordings, which tend to be significantly smaller in magnitude.

Other neuromuscular response measurements are also known in the art. By way of example but not limitation, such neuromuscular response measurements include A-waves, axon reflex, Hoffman reflex, sensory nerve action potential (or "SNAP"), somatosensory evoked responses, visual evoked responses, auditory evoked responses, etc.

It is believed that neuropathology alters these other neuromuscular response measurements as well. As a result, analyzing these other neuromuscular response measurements can also be useful in detecting such neuropathology.

SUMMARY OF THE INVENTION

The present invention comprises a method and apparatus for the detection of neuromuscular disease using disease specific evoked neuromuscular response analysis.

More particularly, in one form of the invention there is provided a method for assessing neuromuscular pathology in an individual, comprising the steps of:

(a) applying a plurality of stimuli to a peripheral nerve;

(b) recording from the peripheral nerve, or from a muscle innervated by the peripheral nerve, at least one response to each stimulus;

(c) processing each response into at least one response characteristic;

(d) compiling the response characteristics from all of the responses into a plurality of descriptive parameters of the response characteristics; and (e) analyzing the plurality of descriptive parameters according to a function specific to the neuromuscular pathology so as to yield an indicator of the pathology.

In another form of the invention, there is provided apparatus for assessing neuromuscular pathology in an individual, the apparatus comprising:

(a) a stimulator for activating a peripheral nerve;

(b) one or more recording channels for recording evoked responses from the peripheral nerve, or from a muscle innervated by the peripheral nerve; and (c) a processor for processing the responses into a plurality of F-wave response characteristics, compiling the response characteristics into a plurality of descriptive parameters, operating on the descriptive parameters with a function that is specific to the neuromuscular pathology so as to yield a disease indication, and analyzing the disease indication in order to assess the existence or progression of the neuromuscular pathology.

In another form of the invention, there is provided a method for the determination of a function whose output indicates neuromuscular pathology in an individual, the method comprising the steps of:

(a) recording, from a peripheral nerve, or from a muscle innervated by a peripheral nerve, a plurality of responses evoked by a plurality of stimuli delivered to the peripheral nerve;

(b) processing each of the responses into at least one response characteristic;

(c) compiling the response characteristics from all of the responses into a plurality of descriptive parameters;

(d) repeating steps (a), (b) and (c) on a plurality of individuals without a specific neuromuscular pathology so as to generate a first set of the descriptive parameters;

(e) repeating steps (a), (b) and (c) on a plurality of individuals with a specific neuromuscular pathology so as to generate a second set of the descriptive parameters; and (f) processing the first set of descriptive parameters and the second set of descriptive parameters so as to determine a function of the descriptive parameters which is indicative of the specific neuromuscular pathology.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 2 illustrates correspondence of MRI and nerve conduction findings in a 41-year-old man with three months of radiating right-sided leg pain and numbness. The patient exhibited a positive straight leg raise test, normal ankle and patellar reflexes, and had no sensory loss or weakness. A body symptom diagram revealed pain in the posterior thigh and leg, and numbness in portions of the L5 and S1 dermatomes. The T2-weighted axial image (TR/TE, 4400/102 msec) at the L5-S1 intervertebral disc space level shows a broad based posterior and right paramedian protrusion (white arrow) compressing the thecal sac and the right S1 nerve root sleeve at its origin. Peroneal nerve traces show F-wave responses to forty sequential stimuli with clear prolongation of latencies (short vertical lines) beyond expected range (long vertical lines, mean±2 stdev) based on the subject's height. The F-wave amplitude scale (the short vertical line to the right of the traces) is 1 mv.

FIG. 8 is a table showing the demographic, clinical and MRI features of the study groups.

DETAILED DESCRIPTION OF THE PREFERRED EMBODIMENTS

Introduction

The present invention has application to the diagnosis of a wide range of different neuromuscular pathologies.

For the purposes of example but not limitation, the present invention will hereinafter generally be discussed in the context of a composite nerve conduction measurement for the detection of lumbosacral nerve root compression. However, it should be appreciated that this discussion is intended to be exemplary in nature, and that the present invention may be applied to, and is in fact intended to be applied to, the diagnosis of a wide range of other neuromuscular and neurological pathologies, e.g., upper extremity nerve entrapment syndromes, diabetic neuropathy, nerve compression, nerve transection, nerve root compression, biochemical nerve root dysfunction, systemic nerve disease, ALS, multiple sclerosis, Alzheimer's disease, dementia, polyneuropathies, etc.

General Methodology

Figure 4:
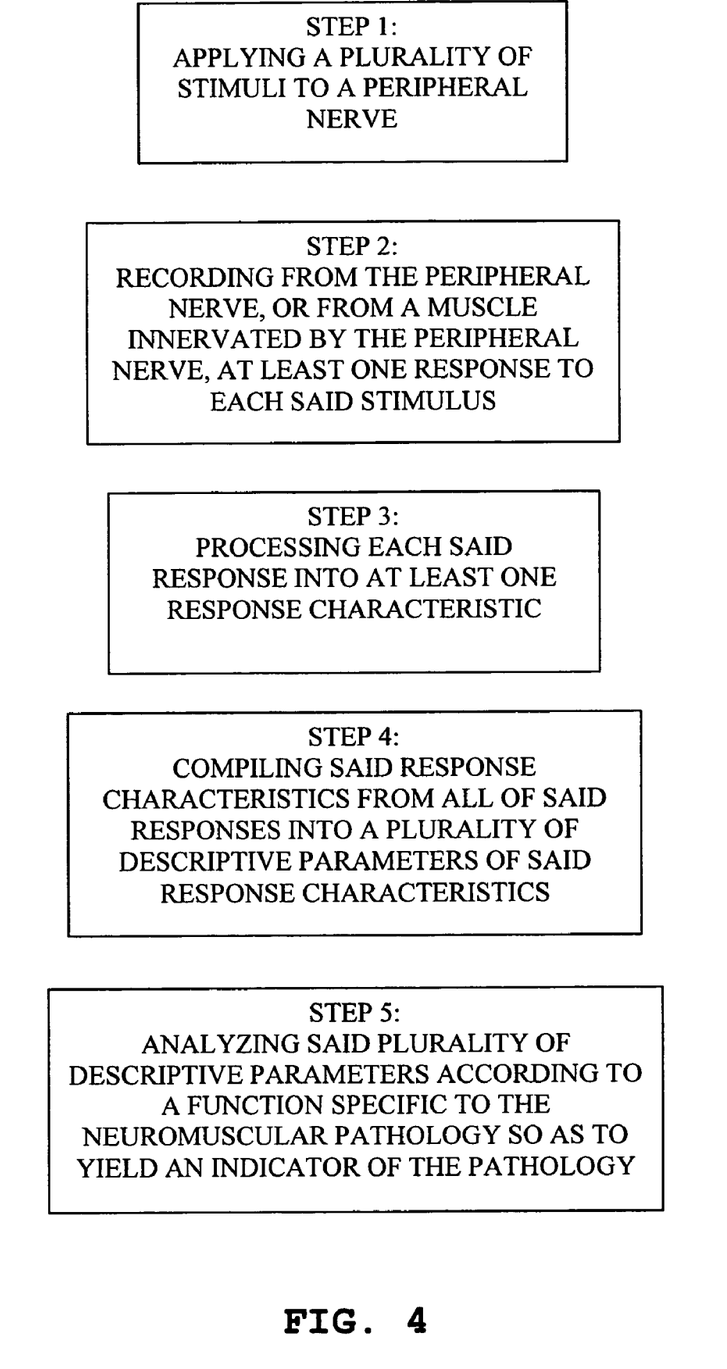
FIG. 4 is a flowchart representing a method of the present invention.

In accordance with the present invention and as shown in FIG. 4, the neuromuscular pathology in an individual is assessed by:

(a) applying a plurality of stimuli to a peripheral nerve;

(b) recording from the peripheral nerve, or from a muscle innervated by the peripheral nerve, at least one response to each stimulus;

(c) processing each response into at least one response characteristic;

(d) compiling the response characteristics from all of the responses into a plurality of descriptive parameters of the response characteristics; and (e) analyzing the plurality of descriptive parameters according to a function specific to the neuromuscular pathology so as to yield an indicator of the pathology.

Figure 5:
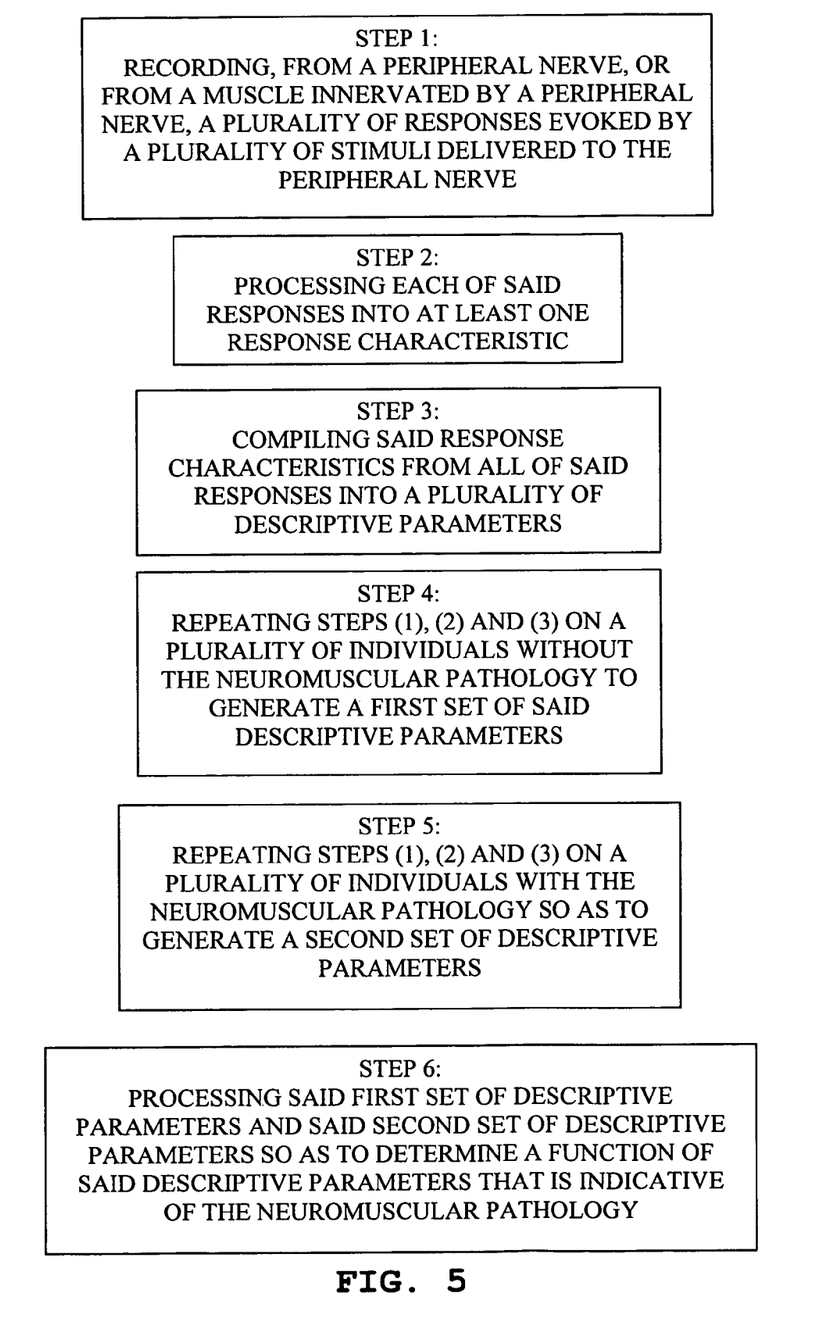
FIG. 5 is a flowchart representing a method of the present invention.

Another form of the invention is illustrated in FIG. 5.

Depending on the particular neuromuscular pathology involved, the response being tracked may relate to CMAP, F-waves, A-waves, axon reflex, Hoffman reflex, sensory nerve action potential, somatosensory response, visual evoked response, auditory evoked response, etc.

And, depending on the particular neuromuscular pathology involved, the response characteristic being tracked may relate to latency, amplitude, duration, area, morphology, persistence, complexity, entropy, etc.

And, depending on the particular neuromuscular pathology involved, the descriptive parameter of the response characteristic may relate to deciles, other percentiles, mean, median, minimum, maximum, variance, standard deviation, absolute deviation, high order statistics, etc.

Lumbrosacral Nerve Root Compression

Lumbrosacral nerve root compromise is an important consideration in the differential diagnosis of low back and leg pain. Nerve root involvement is characterized by radiating pain and segmental sensory-motor abnormalities, and may be confirmed with radiologic and electrodiagnostic studies. These two diagnostic modalities appraise complementary aspects of nerve root pathology. Imaging studies visualize structural abnormalities from which neurological sequela may be inferred; however, they are also associated with high false positive rates. Electrodiagnostic methods include needle electromyography ("nEMG"), somatosensory evoked potentials ("SEP") and nerve conduction studies ("NCS"). These methods assess the physiological integrity of the nerve roots and have the added benefit of sensitivity to non-structural root disease, lower extremity neuromuscular pathology and systemic neuropathies.

In-office NCS are used in the evaluation of patients with upper extremity muscoskeletal complaints. Analogous clinical value can be gained in the assessment of patients presenting with low back and leg symptoms. However, prior applications of nerve conduction measurements to the detection of nerve root compromise have used widely varying methodologies that were not optimized to the specific pathophysiological characteristics of this disease.

In accordance with the present invention, a novel composite nerve conduction measurement is determined that is designed specifically for the detection of lumbosacral (L5, S1 or both) nerve root compression.

Materials and Methods

Subject Selection. The L5/S1 compression group was drawn from patients referred to outpatient MRI centers for evaluation of back and/or leg symptoms. Among this population, patients 18 to 75 years of age with MRI-confirmed L5, S1 or dual nerve root compression secondary to lumbosacral disc disease were eligible to participate in the study if they had lower extremity symptoms during the prior 30 days (relative to the date of the MRI study), including a majority of the past 7 days, and no history of an invasive spinal procedure. Individuals with a history of non-dermal malignancy, diabetes, lower extremity neuromuscular conditions, polyneuropathy or current pregnancy were excluded. The first thirty-five patients who satisfied these criteria were enrolled in the study. At the time of electrophysiological testing, each subject completed a diagram that documented the location and character of symptoms and a questionnaire concerning medical and demographic risk factors. Patients with bilateral symptoms indicated which side was more severely affected. In addition, an abbreviated physical examination was performed that included patellar and ankle reflexes, assessment of sensory loss in the lower leg and foot, and evaluation of dorsiflexion, plantarflexion, eversion and inversion weakness of the foot.

The control group consisted of asymptomatic individuals, between 18 and 75 years of age, drawn from the local community who had no history of back or leg symptoms in the prior year, diagnostic imaging of the neck or back, lower extremity NCS in the past year, prior diagnosis of radiculopathy or invasive procedures of the spine. Individuals with a history of non-dermal malignancy, diabetes, lower extremity neuromuscular conditions, polyneuropathy or current pregnancy were excluded. The first thirty-five subjects who satisfied these criteria were enrolled as controls.

MRI Evaluation. Imaging was performed using standard MRI imaging protocols for evaluation of lumbosacral radiculopathy. Axial images were obtained at the L3-L4 through L5-S1 intervertebral disc space levels. All studies were evaluated for evidence of lumbar intervertebral disc herniation and nerve root compression. The degree of nerve root compression was graded for severity by a radiologist blinded to the electrophysiological results. Mild compression was defined as contact with the nerve root and/or mild distortion of the nerve root sheath, moderate compression was defined as marked distortion of the nerve or nerve root sheath and/or slight displacement of the nerve root, and severe compression was defined as marked displacement of the nerve root or nerve root sheath.

Figure 6:
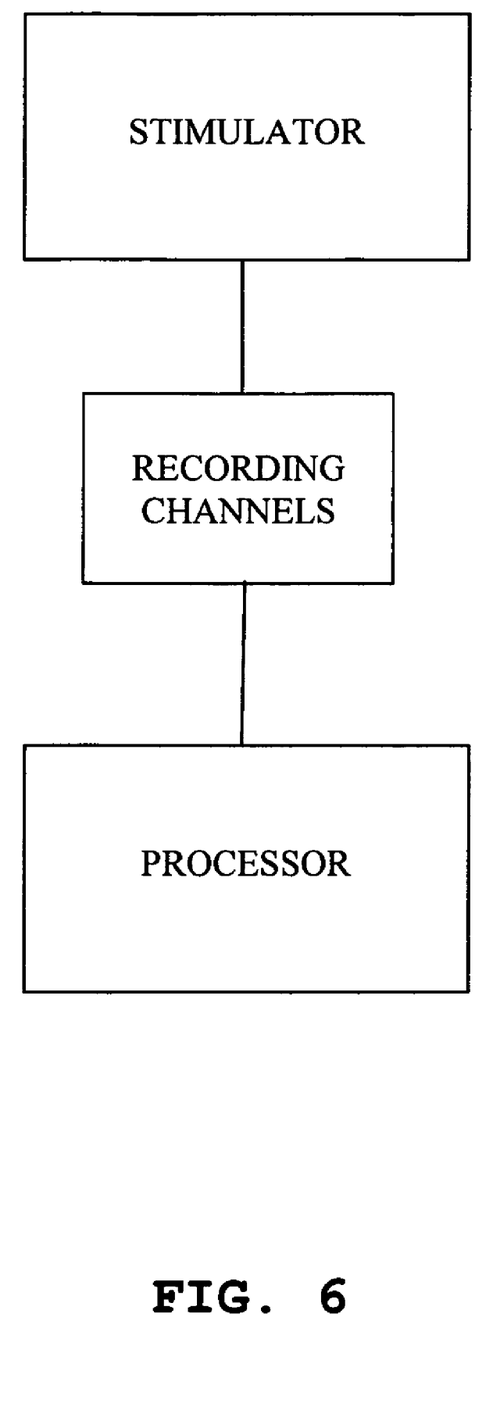
FIG. 6 is a schematic view representing an apparatus of the present invention.
Figure 7:
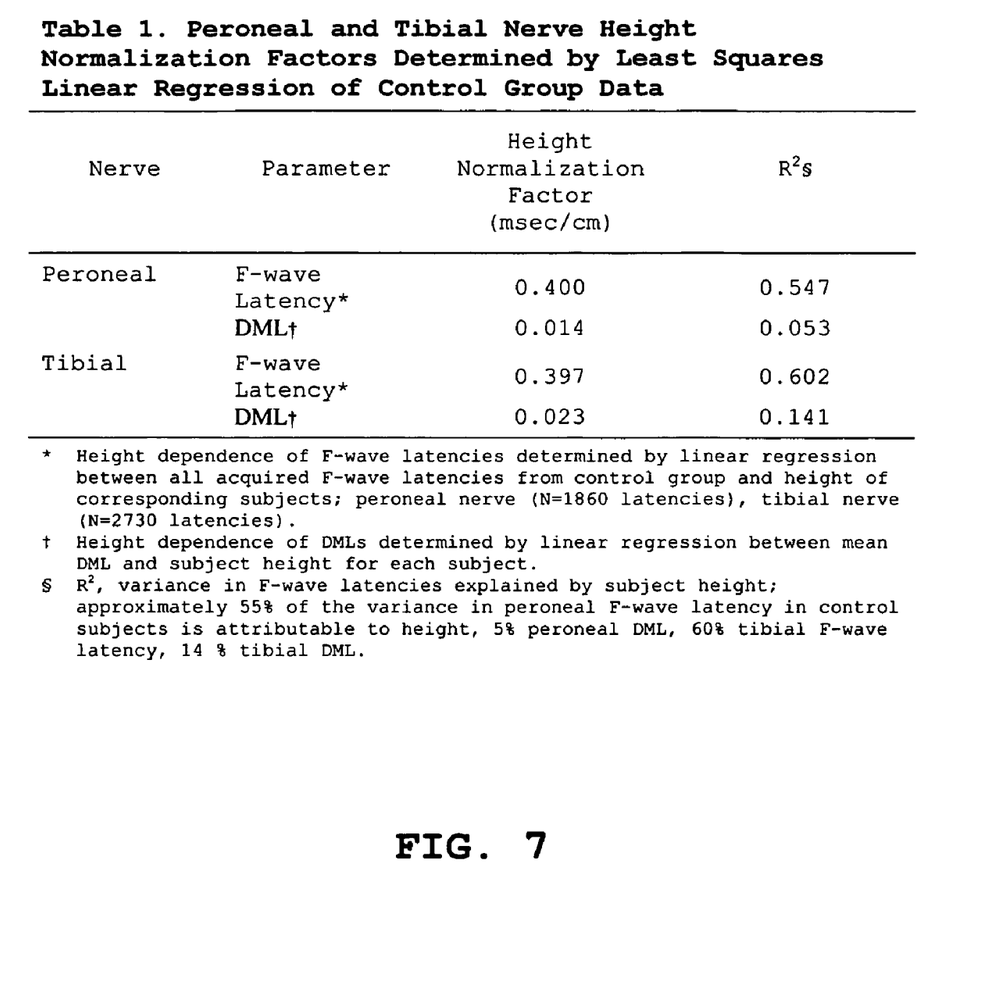
FIG. 7 is a table showing the peroneal and tibial nerve height normalization factors of the Control Group data which were determined by Least Squares Linear Regression.

Electrodiagnostic Evaluation. The posterior tibial ("tibial") and deep peroneal ("peroneal") nerves were evaluated bilaterally in all study subjects using standard nerve conduction procedures. Forty CMAPs and F-wave responses were measured from the extensor digitorum brevis and abductor hallucis for each peroneal and tibial nerve, respectively. All acquired data were stored for subsequent signal processing and data analysis. Subjects in the L5/S1 compression group were evaluated within two weeks of their MRI study and prior to any surgical intervention. The electrophysiological measurements were performed with an automated nerve conduction monitoring device (i.e., the NC-stat® device manufactured by NeuroMetrix, Inc. of Waltham, Mass.). See FIG. 6. For each subject, all recorded traces were presented graphically to an experienced waveform assignment expert who was blinded to the radiological, clinical, demographic and anthropometric characteristics of the subject. The expert determined the distal motor latency ("DML") and CMAP amplitude from an averaged CMAP response, and assigned a latency and amplitude to all F-wave responses within each trace. All nerve conduction parameters were normalized to a subject height of 172 cm (approximately 5'8"). Height normalization factors were determined from the control group by performing a least squares linear regression between subject height and each nerve conduction parameter, with the exception of F-wave persistence. The normalization factors were defined as the slope of the respective best-fit lines (see Table 1). These values are slightly larger than previously published height normalization factors.

Data Analysis. NCS are typically graded as abnormal if any measured parameter falls outside its respective reference range. In accordance with the present invention, the approach taken in this analysis was to define a composite measurement, i.e., the "NC-composite", that integrates multiple nerve conduction parameters predictive of lumbosacral nerve root compression into a single index. The purpose of this measurement was to identify pathology in either root rather than to localize the specific root involved, although the same techniques can be applied to identify pathology in a specific root if desired.

The general form of the NC-composite index is shown in Equation 1 below:

$$NC_{composite} = e^{\frac{\sum_{i=1}^{N} \alpha_i p_i}{1 + \sum_{i=1}^{N} \alpha_i p_i}} \tag{1}$$

where N represents the total number of predictive nerve conduction parameters, $p_i$ is the i-th nerve conduction parameter value and $\alpha_i$ is a corresponding weighting coefficient. The parameters and coefficients were determined by backwards stepwise multivariate logistic regression analysis (using the SYSTAT 10™ software made by SPSS Inc. of Chicago, Ill.) against a dependent variable designating subject membership in the control or L5/S1 compression groups. At each iteration of the logistic regression, the least significant parameter (largest p value) was removed and the regression repeated. The peroneal and tibial nerve conduction parameters were first analyzed separately until all remaining parameters met a preliminary significance criteria (p<0.1). The initially significant parameters from both nerves were then combined, and the stepwise regression continued, until a final significance criteria (p<0.05) was achieved for all remaining parameters. For each nerve the following parameters were initially included: minimum F-wave latency, mean F-wave latency, maximum F-wave latency, $1^{st}$ through $9^{th}$ F-wave latency deciles, F-wave persistence, DML and CMAP amplitude. The utilization of latency deciles is a novel approach that minimizes a priori assumptions about the F-wave latency distribution shape or its most diagnostically relevant features.

In the foregoing discussion, the NC-composite was derived using backwards stepwise multivariate logistic regression analysis. However, it should also be appreciated that other techniques may also be used, such as other logistic regression techniques, the use of neural networks, linear discriminate analysis, linear multivariate regression, clustering, etc.

The accuracies of the NC-composite and a performance reference (i.e., the peroneal minimum F-wave latency which is the most common F-wave parameter reported in traditional NCS) were assessed by the diagnostic sensitivity at a fixed specificity of 85% and by non-parametric receiver operating characteristic ("ROC") curve analysis. A specificity of eighty-five percent exceeds that of most diagnostic modalities used in the assessment of spinal pathology and low back pain. The area under the non-parametric ROC curves summarizes diagnostic accuracy and is interpreted as the probability that an affected subject selected at random will have a more abnormal result than a randomly selected control. This probability can be converted into an odds value so that the relative diagnostic accuracy of two ROC curves can be compared as an odds ratio (or "OR"). By way of example, an OR of 2 would suggest that the NC-composite was twice as effective as the performance reference. Ninety-five percent confidence intervals ("CIs") for the sensitivity, area under the ROC curve, and ORs were determined with the bootstrap method using the MATLAB™ 5.3 software made by MathWorks of Natick, Mass.

Results

A total of 105 limbs were studied electrophysiologically, seventy limbs (35 subjects) in the control group and thirty-five limbs (35 subjects) in the L5/S1 compression group. In the latter group, only the most symptomatic limb was evaluated. The L5/S1 compression group was further refined to twenty-five limbs by excluding subjects without appropriate segmental abnormalities (one subject), a history of prior surgery revealed after study (one subject), unobtainable peroneal and tibial motor responses (four subjects), and incomplete electrophysiological studies. (four subjects, two because of electrical interference and two because of inability to tolerate stimuli). The data for one additional subject with a missing tibial response (secondary to pedal edema) was included in all analyses except those requiring both nerve values. As shown in Table 2, gender, height and age were well matched between the two groups. Only age showed a statistically significant difference (two sample t-test; p<0.05), although the range was similar. Controls were less likely to be female (34.3% vs. 48%), although this discrepancy was not statistically significant given the number of subjects in the study (chi-square test). Most of the nerve root compression group subjects (84%) reported experiencing "low back pain". On physical examination, the most frequent findings were a positive straight leg raise test (68%), diminished ankle reflexes (44%), sensory loss (32%) and weakness (28%). The most common pattern of nerve root involvement was an isolated compression of L5 (9 limbs, 36%) or S1 (9 limbs, 36%), with the remaining subjects demonstrating compromise of both L5 and S1 (7 limbs, 28%). Using MRI criteria, 25% of L5 roots and 37.5% of S1 roots were graded as severely compressed. Three of the four subjects with unobtainable motor nerve responses had severe spinal root compression by MRI examination and either weakness or sensory loss on physical examination.

Figure 3:
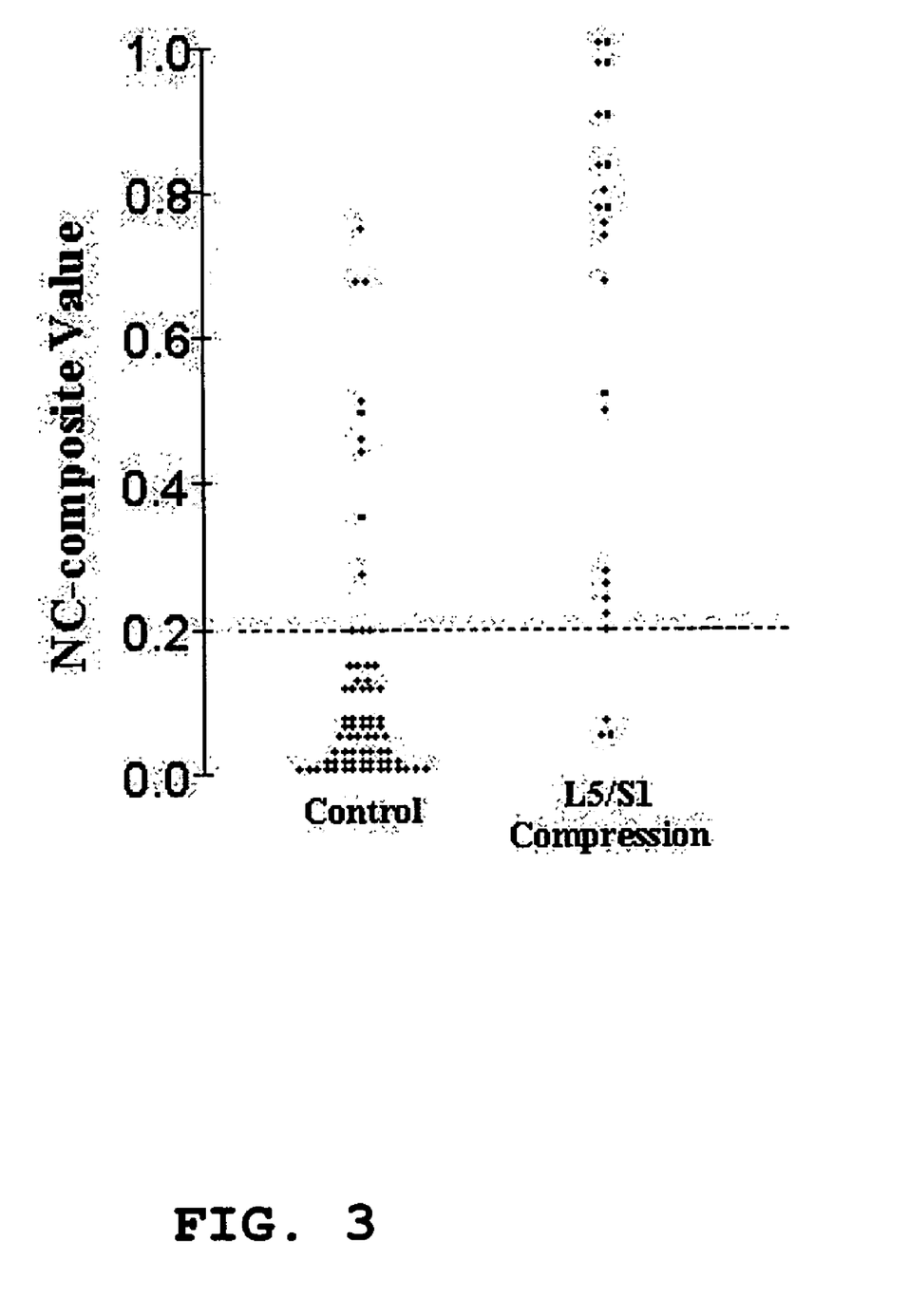
FIG. 3 illustrates NC-composite values for control and L5/S1 nerve root compression groups. The majority of control values fall below the 0.2 level, while the opposite is true for the L5/S1 group.
Figure 9:
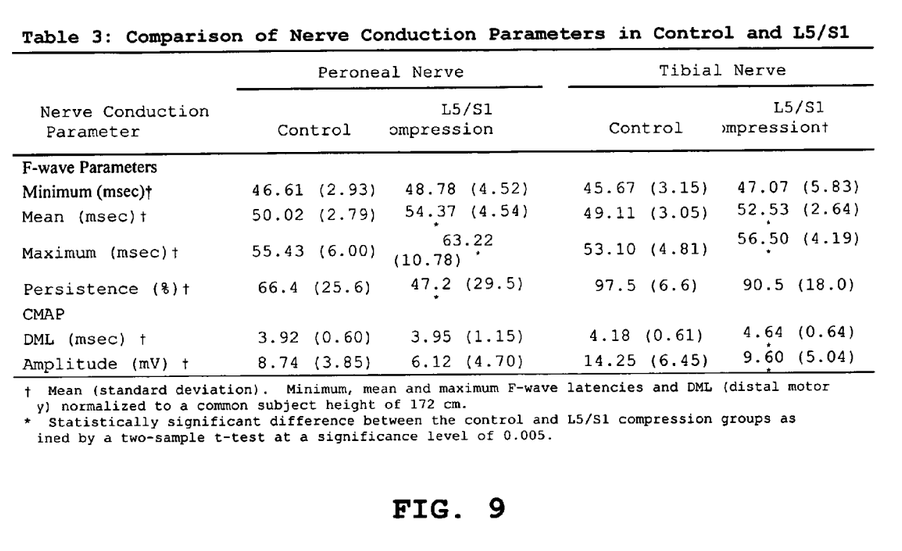
FIG. 9 is a table showing the comparison of nerve conduction parameters in the Control Group and the L5/S1 Group.
Figure 10:
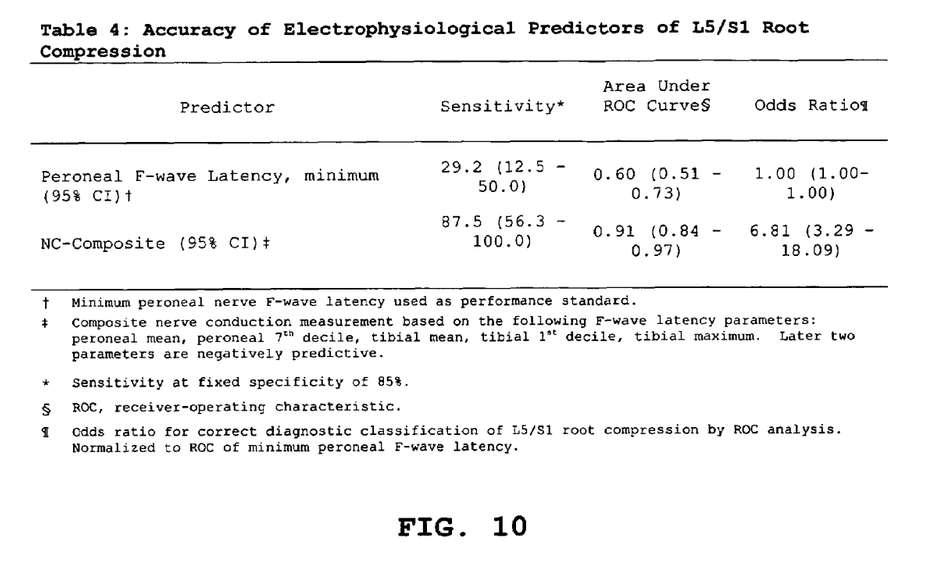
FIG. 10 is a table showing the accuracy of electrophysiological predictors of L5/S1 root compression.

Table 3 compares nerve conduction measurements in the control and L5/S1 compression groups. Among F-wave latency parameters, the mean and maximum latencies were significantly different for both the peroneal and tibial nerves (p<0.005, two sample t-test). In addition, peroneal persistence, tibial DML and tibial CMAP amplitude demonstrated statistically significant differences (p<0.005, two sample t-test) between the two groups. Notably, the peroneal and tibial minimum F-wave latencies did not reach statistical significance. FIG. 3 shows an example of the correspondence between MRI and nerve conduction findings in a subject from the L5/S1 compression group. In multivariate logistic regression analysis, the significant predictors of nerve root compression were the peroneal mean F-wave latency (coeff=−0.933, OR=0.39, 95% CI, 0.16 to 0.97), peroneal $7^{th}$ F-wave latency decile (coeff=1.059, OR=2.88, 95% CI, 1.25 to 6.64), the tibial mean F-wave latency (coeff=2.417, OR=11.22, 95% CI, 2.35 to 53.51), the tibial $1^{st}$ F-wave latency decile (coeff=−0.967, OR=0.38, 95% CI, 0.15 to 0.99), and the tibial maximum F-wave latency (coeff=0.920, OR=0.40, 95% CI, 0.22 to 0.72). These results indicate that, in combination, the peroneal $7^{th}$ F-wave latency decile and the tibial mean F-wave latency are positively predictive of nerve root compression while the other three parameters are negatively predictive of nerve root compression. The NC-composite measurement constructed from these five parameters had an area under the ROC curve of 0.91 (95% CI, 0.84 to 0.97, Table 4). By comparison, the peroneal minimum F-wave latency, which is the F-wave parameter most often reported in traditional nerve conduction studies, had an ROC area of 0.60 (95% CI, 0.51 to 0.73). As shown in FIG. 3, the majority of control NC-composite values fell below 0.2 while the opposite was true for the L5/S1 compression group. At a fixed specificity of 85%, the NC-composite had a diagnostic sensitivity of 87.5% (95% CI, 56.3 to 100.0, Table 4) while the peroneal minimum F-wave latency had a sensitivity of 29.2% (95% CI, 12.5 to 50.0, Table 4). Expressed as an odds ratio (OR), the NC-composite measurement had an OR for detection of nerve root compression of 6.81 (95% CI, 3.29 to 18.09, Table 4) relative to the peroneal minimum F-wave latency.

Discussion

The high prevalence of low back pain has motivated the development of various diagnostic modalities. The use of nerve conduction measurements for this application has several key advantages. First, the F-wave component of the nerve conduction study directly examines the electrophysiological function of the anterior L5 and S1 roots and indirectly the corresponding dorsal roots due to local neural interactions between the dorsal root ganglia and motor neurons. Second, nerve conduction measurements can help exclude peripheral neuropathies with clinical characteristics that overlap with nerve root compromise. Finally, the application of in-office nerve conduction measurements for detection of nerve root compression may allow early triage into directed therapy, help resolve discrepancies between clinical and imaging findings, identify non-mechanical root irritation such as those secondary to the inflammatory effect of damaged or dislodged nucleus pulposus, demonstrate physiological response to operative treatment, and may have value in predicting outcomes of therapeutic interventions.

There is no widely accepted "gold standard" definition for nerve root compression due to a lack of standardization in surgical descriptions. In this analysis, a surrogate marker was used that required explicit MRI evidence of root compression and consistent segmental sensory abnormalities. The control subjects, all of whom denied low back and leg symptoms, did not have MRI studies performed. Due to the relatively high prevalence of disc abnormalities in asymptomatic individuals, it is possible that several would have had superfluous radiological evidence of disc abnormalities and potentially root involvement. With the aforementioned case definition for nerve root compression, multivariate logistic regression identified a combination of five F-wave latency parameters that was predictive of lumbosacral root compression: peroneal mean latency, peroneal $7^{th}$ latency decile, tibial mean latency, tibial $1^{st}$ latency decile, and tibial maximum latency. The NC-composite measurement was constructed from these five parameters. Although the purpose of this measurement was to identify pathology in any lumbosacral root (L5, S1 or both) rather than to localize the specific root involved, similar techniques can be applied to the localization problem. It is interesting to note that although the peroneal and tibial minimum F-wave latencies are the most commonly reported F-wave latency parameters, neither was predictive of root compression when combined with the five parameters noted above. In accordance with other studies and standard clinical practice, distal nerve measurements (i.e. DML and CMAP amplitude) were not predictive of root involvement and were not included in the NC-composite. However, in a population with more severe disease, these measurements may be clinically valuable. In ROC analysis, the NC-composite exhibited an area under the ROC curve of 0.91. A value over 0.90 is considered indicative of a highly accurate test. At a specificity of 85%, the sensitivity was 87.5%. This level of diagnostic specificity exceeds that of MRI and other radiological modalities, which are generally found to have false positive rates of 40-60% in adult asymptomatic populations. Inasmuch as the determination of diagnostic sensitivity was based on MRI confirmed root compression, the false negative rate of NC-composite is low and essentially equivalent to MRI in this study group. Due to variations in electrodiagnostic methods and nerve root compression case definitions, it is difficult to compare these results directly to prior reports. Nevertheless, these diagnostic performance levels exceed those reported in most previous studies of nerve conduction measurements and are comparable to needle EMG (i.e., nEMG) with respect to both sensitivity and specificity.

The discrepancy among reports on the accuracy of nerve conduction measurements in identifying nerve root compression has been interpreted by some to suggest that the diagnostic technique is inherently limited in this application. However, these conclusions did not adequately account for critical differences in methodology amongst the studies. Most studies were limited to an analysis of minimum F-wave latencies which are likely to miss mild disease because they represent conduction of the healthiest nerve fibers and roots. In the present analysis, the NC-composite had 6.81-fold greater diagnostic accuracy than peroneal minimum F-wave latency. At a fixed specificity of 85%, the sensitivity of the NC-composite was 87.5% while that of the peroneal minimum F-wave latency was 29.2%.

The efficacy of the NC-composite measurement is derived from a number of factors. First, all of the parameters are normalized to account for their dependence on subject height, which is often overlooked despite its relevance to diagnostic sensitivity. Second, because of the relationship between F-wave number and diagnostic reliability, forty F-wave responses were obtained for each nerve as opposed to smaller numbers employed in routine clinical use and prior studies. Third, this analysis clarifies that the peroneal and tibial nerves carry non-redundant diagnostic information about L5 and S1 root compression. These findings are consistent with the myotomal distribution of the two nerves. Finally, the NC-composite integrates multiple nerve conduction parameters in a statistically optimal manner, thereby creating greater potential for detecting the neurophysiological impact of the complex mechanical and biochemical events associated with nerve root compromise.

Application to Other Neuromuscular Disease

In the foregoing discussion, the evoked neuromuscular response analysis was applied in the context of detecting lumbrosacral nerve root compression. However, the present invention may also be applied to the detection of other neuromuscular disease. By way of example but not limitation, the present invention can be applied to the diagnosis of neuromuscular pathologies such as upper extremity nerve entrapment syndromes, diabetic neuropathy, nerve compression, nerve transection, nerve root compression, biochemical nerve root dysfunction, systemic nerve disease, ALS, multiple sclerosis, Alzheimer's disease, dementia, polyneuropathies, etc. Each such application will involve the establishment of an appropriate NC-composite, based on appropriately weighted descriptive parameters, in accordance with the present invention.

Thus, the neuromuscular pathology in an individual is assessed by:

(a) applying a plurality of stimuli to a peripheral nerve;

(b) recording from the peripheral nerve, or from a muscle innervated by the peripheral nerve, at least one response to each stimulus;

(c) processing each response into at least one response characteristic;

(d) compiling the response characteristics from all of the responses into a plurality of descriptive parameters of the response characteristics; and (e) analyzing the plurality of descriptive parameters according to a function specific to the neuromuscular pathology so as to yield an indicator of the pathology.

Depending on the particular neuromuscular pathology involved, the response being tracked may relate to CMAP, F-waves, A-waves, axon reflex, Hoffman reflex, sensory nerve action potential, somatosensory response, visual evoked response, and auditory evoked response.

And, depending on the particular neuromuscular pathology involved, the response characteristic being tracked may relate to latency, amplitude, duration, area, morphology, persistence, complexity, entropy, etc.

And, depending on the particular neuromuscular pathology involved, the descriptive parameter of the response characteristic may relate to deciles, other percentiles, mean, median, minimum, maximum, variance, standard deviation, absolute deviation, high order statistics, etc.

TABLE 1

Peroneal and Tibial Nerve Height
Normalization Factors Determined by Least Squares
Linear Regression of Control Group Data

| Nerve | Parameter | Height Normalization Factor (msec/cm) | $R^2$§ |
|---|---|---|---|
| Peroneal | F-wave Latency* | 0.400 | 0.547 |
|  | DML† | 0.014 | 0.053 |

TABLE 1-continued

Peroneal and Tibial Nerve Height
Normalization Factors Determined by Least Squares
Linear Regression of Control Group Data

| Nerve | Parameter | Height Normalization Factor (msec/cm) | $R^2$§ |
|---|---|---|---|
| Tibial | F-wave Latency* | 0.397 | 0.602 |
|  | DML† | 0.023 | 0.141 |

*Height dependence of F-wave latencies determined by linear regression between all acquired F-wave latencies from control group and height of corresponding subjects; peroneal nerve (N = 1860 latencies), tibial nerve (N = 2730 latencies).
†Height dependence of DMLs determined by linear regression between mean DML and subject height for each subject.
§$R^2$, variance in F-wave latencies explained by subject height; approximately 55% of the variance in peroneal F-wave latency in control subjects is attributable to height, 5% peroneal DML, 60% tibial F-wave latency, 14% tibial DML.

TABLE 2

Demographic, Clinical, and MRI Features of Study Groups

|  | Control* | L5/S1 Compression† |
|---|---|---|
| No. of Subjects | 35 | 25 |
| Age‡ | 32.7 (8) | 37.4 (8.1) |
| Height (cm)‡ | 172.2 (10.4) | 171.7 (8.13) |
| Female (%) | 34.3 | 48 |
| Low back pain (%)§ | 0 | 84 |
| Left as most symptomatic limb (%)§ | — | 56 |
| Straight leg raise (%)¶ | — | 68 |
| Diminished patellar reflex (%)¶ | — | 8 |
| Diminished ankle reflex (%)¶ | — | 44 |
| Sensory loss (%)¶ | — | 32 |
| Weakness (%)¶ | — | 28 |
| L5 compression/isolated L5 (%)‖ | — | 64/36 |
| L5 compression severe (%)‖ | — | 25 |
| S1 compression/isolated S1 (%)‖ | — | 64/36 |
| S1 compression severe (%)‖ | — | 37.5 |

*Asymptomatic subjects, no history of spine surgery, lower extremity neuromuscular disorders or radiculopathy.
†MRI confirmed L5 and/or S1 root compression, lower extremity symptoms consistent with root involvement. Only those subjects for whom electrophysiological results were obtained are included.
‡Mean (standard deviation)
§Low back pain and symptomatic limb as reported by subject on questionnaire.
¶Straight leg raise, reflexes, sensory loss and weakness determined on physical exam of subject. Positive straight leg raise if increase in distal leg symptoms with hip flexion. Diminished reflexes if less then 2+ using standard clinical methods. Weakness graded as positive if encountered on dorsiflexion, plantarflexion, eversion or inversion of the foot.
‖Based on MRI imaging of lumbosacral spine at L3-L4 through L5-S1 intervertebral disc space levels. Isolated percentage refers to number of patients for which only the L5 or S1 roots were involved. Severe percentage refers to the number of patients with grade III root compression (see Methods).

TABLE 3

Comparison of Nerve Conduction Parameters in Control and L5/S1 Compression Groups

| Nerve Conduction Parameter | Peroneal Nerve | | Tibial Nerve | |
|---|---|---|---|---|
| | Control | L5/S1 Compression | Control | L5/S1 Compression† |
| F-wave Parameters | | | | |
| Minimum (msec)† | 46.61 (2.93) | 48.78 (4.52) | 45.67 (3.15) | 47.07 (5.83) |
| Mean (msec)† | 50.02 (2.79) | 54.37 (4.54)* | 49.11 (3.05) | 52.53 (2.64)* |
| Maximum (msec)† | 55.43 (6.00) | 63.22 (10.78)* | 53.10 (4.81) | 56.50 (4.19)* |
| Persistence (%)† | 66.4 (25.6) | 47.2 (29.5)* | 97.5 (6.6) | 90.5 (18.0) |
| CMAP | | | | |
| DML (msec)† | 3.92 (0.60) | 3.95 (1.15) | 4.18 (0.61) | 4.64 (0.64)* |
| Amplitude (mV)† | 8.74 (3.85) | 6.12 (4.70) | 14.25 (6.45) | 9.60 (5.04)* |

†Mean (standard deviation) Minimum, mean and maximum F-wave latencies and DML (distal motor latency) normalized to a common subject height of 172 cm.
*Statistically significant difference between the control and L5/S1 compression groups as determined by a two-sample t-test at a significance level of 0.005.

TABLE 4

Accuracy of Electrophysiological Predictors of L5/S1 Root Compression

| Predictor | Sensitivity* | Area Under ROC Curve§ | Odds Ratio¶ |
|---|---|---|---|
| Peroneal F-wave Latency, minimum (95% CI)† | 29.2 (12.5-50.0) | 0.60 (0.51-0.73) | 1.00 (1.00-1.00) |
| NC-Composite (95% CI)‡ | 87.5 (56.3-100.0) | 0.91 (0.84-0.97) | 6.81 (3.29-18.09) |

†Minimum peroneal nerve F-wave latency used as performance standard.
‡Composite nerve conduction measurement based on the following F-wave latency parameters: peroneal mean, peroneal 7th decile, tibial mean, tibial 1st decile, tibial maximum. Later two parameters are negatively predictive.
*Sensitivity at fixed specificity of 85%.
§ROC, receiver-operating characteristic.
¶Odds ratio for correct diagnostic classification of L5/S1 root compression by ROC analysis. Normalized to ROC of minimum peroneal F-wave latency.

What is claimed is:

1. A method for the determination of a composite pathology function whose output indicates a neuromuscular pathology in an individual, the method comprising the steps of:
   (a) selecting a first group of individuals that have the neuromuscular pathology;
   (b) applying a plurality of stimuli to a peripheral nerve of each individual in said first group of individuals so as to evoke a plurality of responses to said stimuli from said peripheral nerve or from a muscle innervated by said peripheral nerve;
   (c) recording said responses;
   (d) processing each of said responses into at least one selected response characteristic;
   (e) compiling said at least one response characteristic from all of said responses into a first set of selected descriptive parameters characterizing said first group of individuals;
   (f) selecting a second group of individuals that do not have the neuromuscular pathology;
   (g) repeating steps (b), (c), (d) and (e) on each individual of said second group of individuals that do not have the neuromuscular pathology to generate a second set of said descriptive parameters characterizing said second group of individuals; and
   (h) processing said first and second sets of descriptive parameters so as to determine a composite pathology function of said descriptive parameters that is indicative of the neuromuscular pathology, said composite pathology function being characterized in that the composite pathology function integrates the descriptive parameters into a single index represented by the following equation:

$$NC_{composite} = e^{-\frac{\sum_{i=1}^{N} \alpha_i p_i}{1+\sum_{i=1}^{N} \alpha_i p_i}}$$

where N represents a total number of predictive nerve conduction parameters, $p_i$ is the i-th nerve conduction parameter value and $\alpha_i$ is a corresponding weighting coefficient.

2. The method of claim 1 wherein said processing of said first and second sets of descriptive parameters is performed using logistic regression analysis.

3. The method of claim 1 wherein said processing of said first and second sets of descriptive parameters is performed using an artificial neural network.

4. The method of claim 1 wherein said processing of said first and second sets of descriptive parameters is performed using linear discriminate analysis.

5. The method of claim 1 wherein said processing of said first and second sets of descriptive parameters is performed using linear multivariate regression.

6. The method of claim 1 wherein said processing of said first and second sets of descriptive parameters is performed using clustering.

* * * * *